United States Patent
Ramos

(10) Patent No.: US 11,439,545 B2
(45) Date of Patent: Sep. 13, 2022

(54) DISPOSABLE PANTS

(71) Applicant: Denise Ramos, Teaneck, NJ (US)

(72) Inventor: Denise Ramos, Teaneck, NJ (US)

(*) Notice: Subject to any disclaimer, the term of this patent is extended or adjusted under 35 U.S.C. 154(b) by 209 days.

(21) Appl. No.: 16/028,653

(22) Filed: Jul. 6, 2018

(65) Prior Publication Data
US 2019/0008701 A1    Jan. 10, 2019

Related U.S. Application Data

(60) Provisional application No. 62/529,250, filed on Jul. 6, 2017.

(51) Int. Cl.
*A61F 13/496*  (2006.01)
*A41B 13/04*  (2006.01)
*A61F 13/505*  (2006.01)

(52) U.S. Cl.
CPC ............ *A61F 13/496* (2013.01); *A41B 13/04* (2013.01); *A61F 13/505* (2013.01)

(58) Field of Classification Search
CPC .............. A61F 13/15252; A61F 13/496; A61F 2013/1526; A61F 13/505; A41B 13/04
See application file for complete search history.

(56) References Cited

U.S. PATENT DOCUMENTS

| | | | |
|---|---|---|---|
| 1,577,409 A * | 3/1926 | Rand | A41B 9/04 2/401 |
| 1,664,298 A * | 3/1928 | Katz | A61F 13/72 604/396 |
| 2,032,982 A * | 3/1936 | Gerstman | A41D 1/06 2/228 |
| 2,034,312 A * | 3/1936 | Rubin | A41D 1/06 2/228 |
| 2,418,050 A | 3/1947 | Shank | |
| 2,733,715 A | 2/1956 | Yvette | |
| 3,180,336 A * | 4/1965 | Bett | A41D 10/00 2/80 |
| 3,714,946 A * | 2/1973 | Rudes | A41B 9/12 604/394 |
| 3,828,785 A | 8/1974 | Gamm et al. | |
| 5,057,094 A * | 10/1991 | Abbey | A61F 5/44 604/351 |
| 5,103,501 A * | 4/1992 | Meisels | A41B 9/00 2/104 |

(Continued)

FOREIGN PATENT DOCUMENTS

WO   2013/006113   *   1/2013   ............. A41D 10/00

*Primary Examiner* — Michele M Kidwell
(74) *Attorney, Agent, or Firm* — Boudwin Intellectual Property; Daniel Boudwin

(57) ABSTRACT

A disposable pant that for absorbing liquid and human waste. The disposable pants include an upper section, designed to wrap around a child's waist, a front panel, an opposing back panel, and two side edges located between the front and back panel. Two leg portions are disposed on either side of a crotch area, with fasteners placed on each side edge that are designed to secure the front panel to the back panel. A diaper is in the crotch area, having a pocket designed to absorb solid waste and channels designed to absorb liquid waste. At an end of each leg portion there is an elastic cuff designed to secure each leg portion to an ankle. There is an inner lining inside the pants that is composed of an absorbent material. A child can use the disposable pants as a diaper without ruining a pair of non-disposable pants.

1 Claim, 5 Drawing Sheets

(56) References Cited

U.S. PATENT DOCUMENTS

| | | | |
|---|---|---|---|
| 5,397,318 A * | 3/1995 | Dreier | A61F 13/49009 604/385.19 |
| 5,598,586 A * | 2/1997 | Munjone | A41D 1/089 2/237 |
| 5,876,394 A * | 3/1999 | Rosch | A61F 13/49 604/393 |
| 5,921,974 A * | 7/1999 | Kikuchi | A61F 13/496 604/358 |
| 6,023,789 A * | 2/2000 | Wilson | A41D 1/089 2/228 |
| 6,262,331 B1 * | 7/2001 | Nakahata | A61F 13/49011 604/358 |
| 6,339,847 B1 * | 1/2002 | Hanks | A41B 13/005 2/269 |
| 6,487,727 B1 * | 12/2002 | Harsant | A41D 10/00 2/400 |
| 6,926,702 B1 | 8/2005 | Wilkinson | |
| 7,000,261 B1 * | 2/2006 | Loffredo | A41D 13/1254 2/228 |
| 7,666,174 B2 * | 2/2010 | Onishi | A61F 13/495 604/385.27 |
| 8,214,927 B1 * | 7/2012 | Jondahl | A41D 13/0556 2/228 |
| 8,282,618 B2 * | 10/2012 | Nordness | A61F 13/496 604/396 |
| 2002/0184698 A1 * | 12/2002 | Harris | A41B 9/00 2/400 |
| 2005/0125879 A1 * | 6/2005 | Yang | A61F 13/66 2/228 |
| 2010/0011477 A1 * | 1/2010 | Lee | A41D 27/12 2/46 |
| 2012/0232516 A1 * | 9/2012 | Leon | A61F 13/56 604/386 |
| 2014/0020154 A1 | 1/2014 | Roberts | |
| 2018/0256419 A1 * | 9/2018 | McGilloway | A61F 13/5655 |
| 2019/0142074 A1 * | 5/2019 | Benjamin | A41B 9/002 2/407 |
| 2019/0274373 A1 * | 9/2019 | Meyer | A41D 27/24 |
| 2020/0121520 A1 * | 4/2020 | Sylver | A61F 13/4963 |
| 2020/0237570 A1 * | 7/2020 | Zimering | A61F 13/505 |

* cited by examiner

DISPOSABLE PANTS

CROSS REFERENCE TO RELATED APPLICATIONS

This application claims the benefit of U.S. Provisional Application No. 62/529,250 filed on Jul. 6, 2017. The above identified patent application is herein incorporated by reference in its entirety to provide continuity of disclosure.

BACKGROUND OF THE INVENTION

The present invention relates to disposable pants that are configured to absorb liquid and human waste. More specifically, the present invention provides a diaper disposed in an interior of a pair of disposable pants, wherein the disposable pants are configured to fasten around a user's waist and ankles, and the diaper comprises one or more pockets and a plurality of channels to absorb human waste.

While wearing a diaper, many children will accidentally ruin the pants they are wearing when using the diaper for its intended purpose. However, parents are typically unable to throw the soiled pants away, and must spend time, energy, and resources to find unsoiled clothing and clean the soiled pants. Additionally, if the child is traveling with a parent, the parent is often unable to change the child for an extended period of time, and the child can easily develop sores or rashes if left in a soiled diaper for too long. Further, if a child dirties their pants while traveling, it is unlikely a parent will have an additional change of clothes in the diaper bag. Thus, a pair of pants that can disposably act as a diaper is desired to allow a parent to easily change both the pants and the diaper of a child.

SUMMARY OF THE INVENTION

In view of the foregoing disadvantages inherent in the known types of disposable pants now present in the known art, the present invention provides a disposable pant wherein the same can be utilized for providing convenience for the user when desiring a disposable pant and diaper combination.

It is therefore an object of the present invention to provide a new and improved disposable pant that has all the advantages of the prior art and none of the disadvantages. The disposable pant comprises an upper section configured to encircle the wearer's waist. Additionally, the disposable pant comprises a front panel, an opposing back panel, two side edges disposed between the front and back panel, a crotch area, and two leg receiving portions on either side of the crotch area. Fasteners are disposed on each side edge to allow the front panel to removably secure to the back panel. A diaper is disposed in the crotch area, having one or more pockets configured to absorb solid waste and a plurality of channels configured to absorb liquid waste. A terminal section of each leg portion is an elastic cuff configured to secure each leg portion to an ankle. The disposable pants have an inner lining composed of an absorbent material. In this way, the parent is able to easily change both the pants and the diaper of the child while changing a single garment of clothing.

BRIEF DESCRIPTION OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
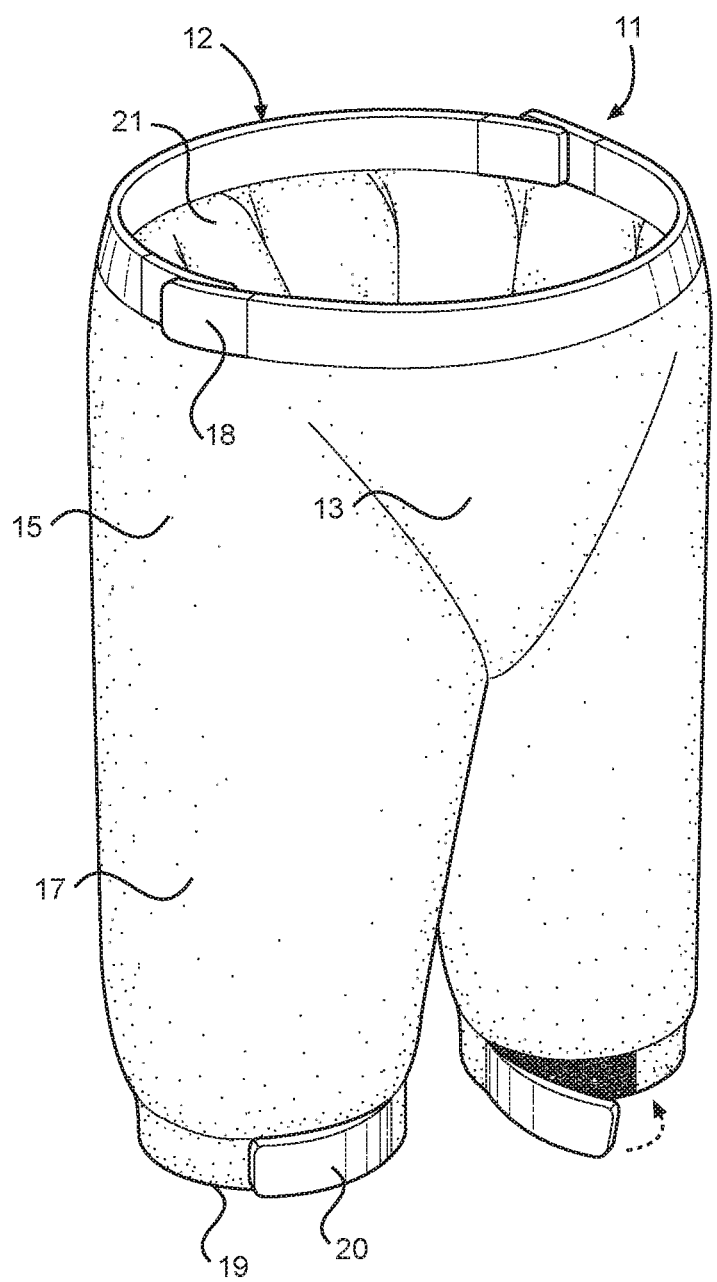
FIG. 1 shows a perspective view of an embodiment of the disposable pants wherein the side panels are fastened.

Reference is made herein to the attached drawings. Like reference numerals are used throughout the drawings to depict like or similar elements of the disposable pants. The figures are intended for representative purposes only and should not be considered to be limiting in any respect.

Figure 2:
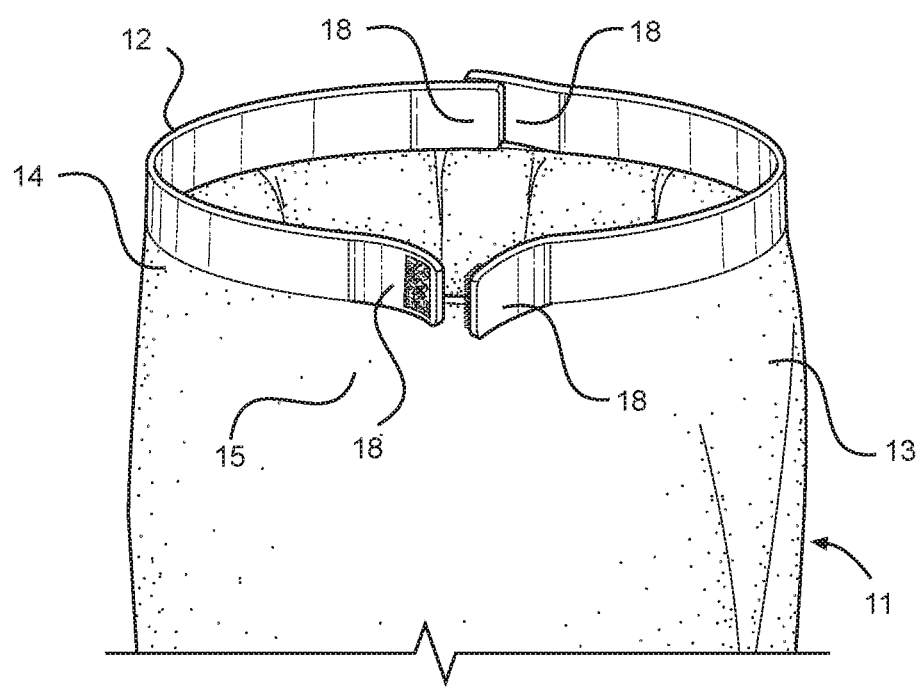
FIG. 2 shows a close-up perspective view of an embodiment of the disposable pants wherein the side panels are unfastened.

Referring now to FIG. 1 and FIG. 2, there are shown perspective views of an embodiment of the disposable pants wherein the side panels are fastened, and wherein the side panels are unfastened. The disposable pants 11 comprise an upper section 12 configured to encircle the wearer's waist 70 (as seen in FIG. 5). The disposable pants 11 further comprise a front panel 13, an opposing back panel and two side edges 15 disposed between the front panel 13 and the back panel. A crotch area is disposed perpendicular to the front panel 13, back panel, and two side edges 15 such that crotch area is disposed along a perimeter of a bottom edge of the front panel 13, back panel, and two side edges 15. Two leg receiving portions 17 are disposed on either side of the crotch area such that the leg receiving portions are aligned with the side panels 15 wherein each leg receiving portion 17 is configured to enclose a leg of a child. In this way, the disposable pants 11 are configured to fully enclose a portion of the legs and a lower torso of a user. Additionally, the disposable pants 11 are composed of a biodegradable material, such that the disposable pants can be recycled when discarded.

A plurality of fasteners 18 are disposed on each of the side edges 15 such that the front panel 13 is removably securable to the back panel 14, thereby enabling an individual to secure the disposable pants 11 such that the upper section 12 encircles the waist of a user. In the illustrated embodiment, the fasteners 18 comprise a hook and loop, however in other embodiments, the fasteners 18 comprise snaps, magnets, or another suitably secure fastener. In one embodiment, the upper section 12 configured to encircle the waist of the user is composed of an elastic material such that is it configured to removably secure to the waist of the user, thereby aiding the fasteners 18. In another embodiment, the elastic material is used without the fasteners 18.

The leg portions 17 of the disposable pants comprise a terminal section 19 ending in an elastic cuff configured to secure each leg portion 17 to a legged body part 71, such as an ankle, of the user. In one embodiment, the terminal section 19 is configured to fasten around a calf or a knee of a user, however in the shown embodiment the leg portion 17 extends to an ankle of the user. In the illustrated embodiment, the terminal section 19 further comprises one or more leg fasteners 20 configured to additionally aid in securing the leg portion 17 to the body of the user in case the elasticity wears out. In the shown embodiment, the leg fasteners 20 comprise a hook and loop, however in alternate embodiments, snaps, magnets or another suitably secure fastener is used. In the illustrated embodiment, the disposable pants 11 are configured for a toddler. However, in alternate embodiments, the disposable pants 11 are configured for additional sizes of users, such as an infant or a young child.

Figure 3A:
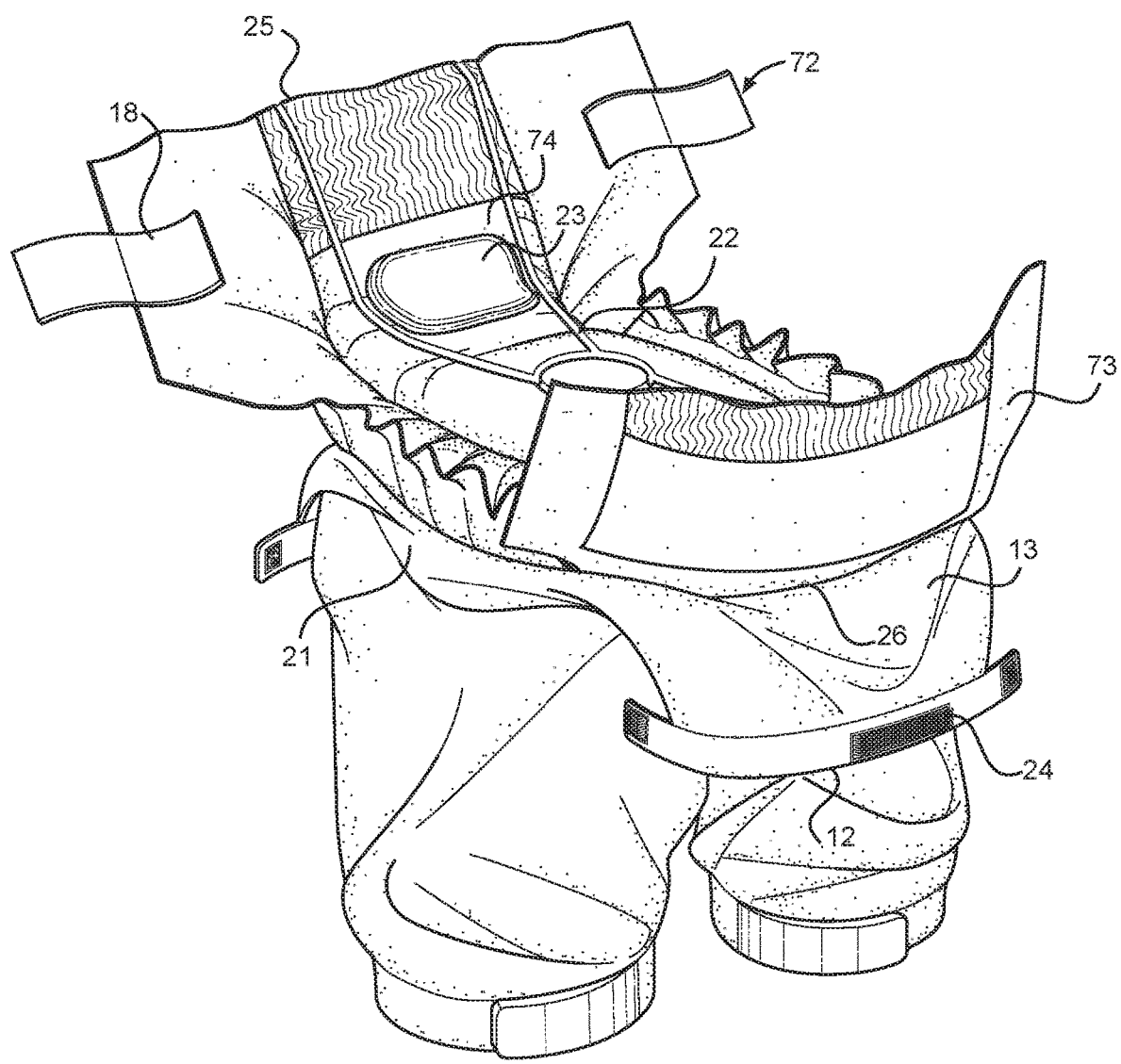
FIG. 3A shows a perspective view of an embodiment of the disposable pants having a diaper inserted therein.
Figure 3B:
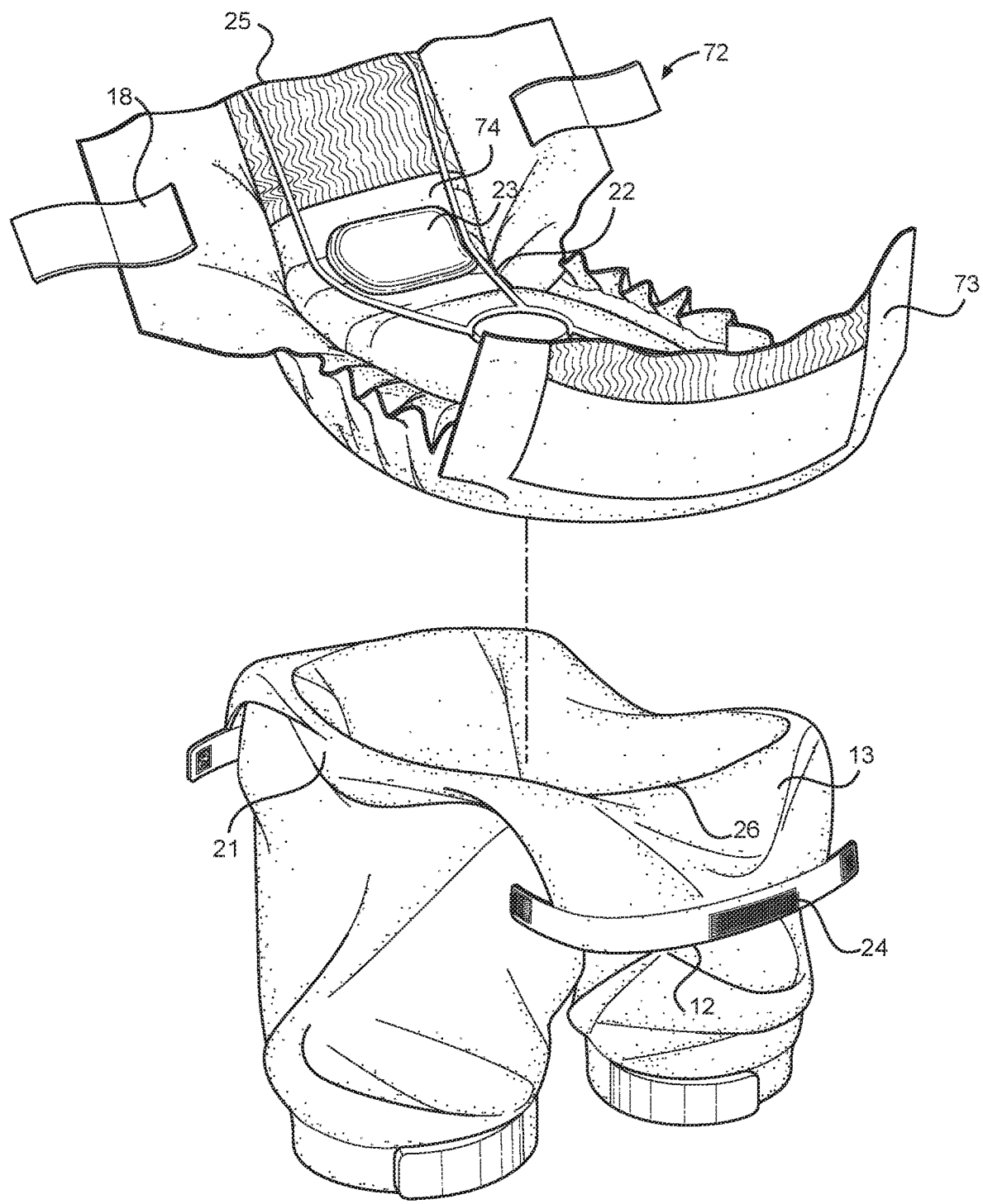
FIG. 3B shows an exploded view of an embodiment of a diaper prior to insertion into the disposable pants.

Referring now to FIG. 3A and FIG. 3B, there is shown a perspective view of an embodiment of the channels and pocket of the diaper in the disposable pants, and a perspective view of an embodiment of the disposable pants wherein the diaper is removable, respectively. The disposable pants further comprise a diaper 72 disposed within an interior 26 of the disposable pants. The diaper 72 comprises a plurality of channels 22 configured to receive and absorb liquid therein as well as one or more pockets 23 configured to receive and absorb human waste therein.

In the shown embodiment, the plurality of channels 22 comprise grooved indentations extending from a center portion of the diaper 72 towards the front end 73 of the diaper 72 and towards the back end 74 of the diaper 72. In this way, the plurality of channels 22 are embedded within the interior 26 of the disposable pants. In the illustrated embodiment, the plurality of channels 22 extends from the crotch area 16 in to the edge 25 of the diaper 72. However, in another embodiment, the plurality of channels 22 do not extend fully to the edge 25 of the diaper 72. In this way, when a child urinates in the disposable pants 11, the plurality of channels is 22 is configured to conduct the liquid away from the crotch area 16 of the user.

In a similar fashion, the one or more pockets 23 are configured to absorb human waste such that the user is not left with human waste proximal to the skin of the user. In the illustrated embodiment, the pocket 23 is situated at a distal end of the crotch area 16, such that the pocket 23 is disposed proximal to the rear of the child. In the illustrated embodiment, the pocket 23 is a portion of material composed of a substance similar to the plurality of channels 22, wherein the pocket 23 is configured to absorb human waste. As such, the pocket 23 is sized larger than the plurality of channels 22, such that the pocket 23 is configured to encase the majority of the buttocks region of the child. In the illustrated embodiment, the pocket 23 comprises a patch of annularly shaped material disposed between the plurality of channels 22, however in other embodiments the pocket 23 can extend past the plurality of channels 22, such that the plurality of channels 22 extend through the pocket 23.

The disposable pants 11 further comprise an inner lining 21 composed of an absorbent material, such that any liquid and human waste not drawn in by the plurality of channels 22 or pockets 23 is still absorbed. The inner lining 21 comprises the entire inner surface of the disposable pants 11. In the shown embodiment, the inner lining 21 is composed of a hypoallergenic material, thereby decreasing the incidence of rashes along a portion of skin of the user. In one embodiment, the external portion of the disposable pants is composed of a cotton material, however, other suitably non-abrasive materials can be used. In this way, the disposable pants 11 are configured to act as both a diaper and as a pair of pants in a single clothing item.

In one embodiment, the diaper 72 is configured to be removably from the interior 26 of the disposable pants. Thereby, a parent can remove an exterior portion of the pants should they become soiled but the diaper 72 is still usable. In the illustrated embodiment, the upper section 12 comprises one or more front fasteners 24 configured to secure to the diaper 72. The front fasteners 24 are disposed on an interior side of the front panel 13 along the upper section 12, wherein the front fastener 24 is configured to receive the front end 73 of the diaper 72. Further, one or more rear fasteners are disposed on an interior side of the back panel along the upper section 12, such that the rear fastener is disposed to mirror the front fastener 24. Similarly, the rear fastener is configured to receive a back end 74 of the diaper 72. In the illustrated embodiment, the front fastener 24 and the rear fastener comprise a hook and loop, however any suitable fastener, such as an adhesive, can be used, thereby allowing the diaper 72 to be removably secured to the interior 26 of the disposable pants. In another embodiment, the front fastener 24 and the rear fastener each comprise a pair of apertures, wherein the apertures are disposed on the front panel 13 and opposing back panel respectively and configured to receive the fasteners 18 therethrough such that the diaper 72 is removably affixed to the disposable pants.

Figure 4:
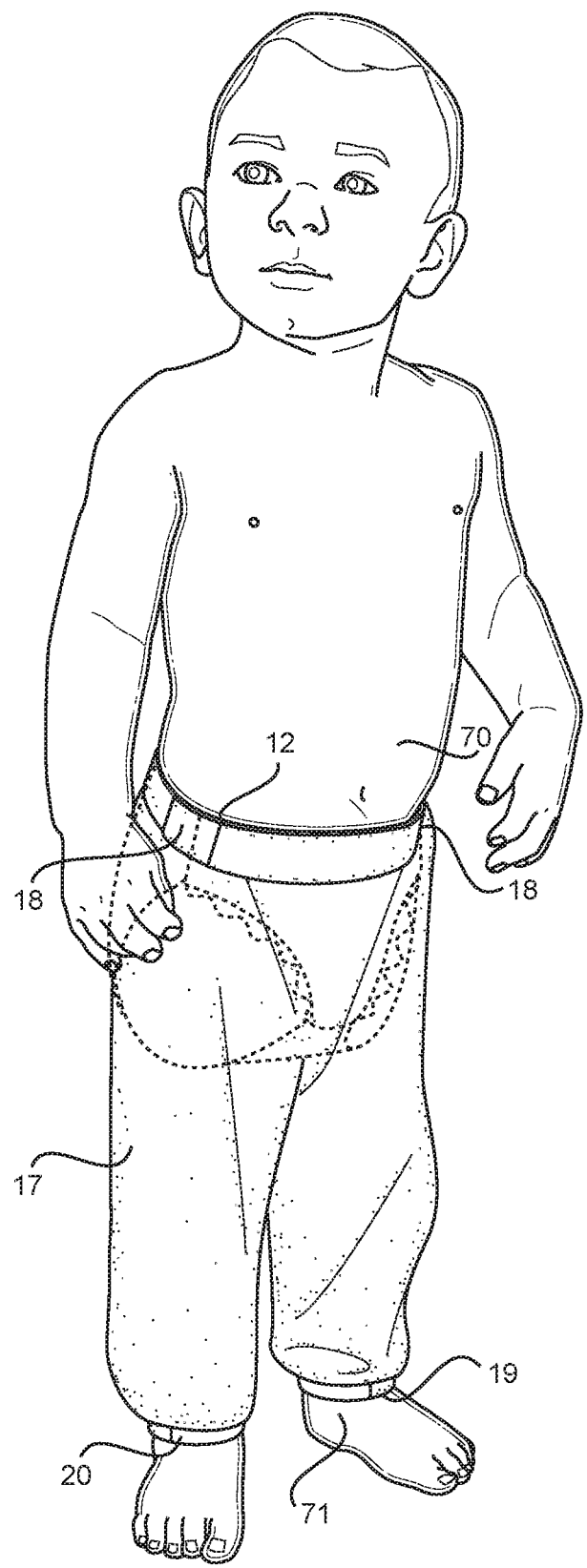
FIG. 4 shows a perspective view of an embodiment of the disposable pants worn by a child wherein the side panels and leg portions are fastened.

Referring now to FIG. 4, there is shown a perspective view of an embodiment of the disposable pants worn by a child wherein the side panels and leg portions are fastened. In operation, a user, such as a child, will wear the disposable pants in place of a diaper and regular pants. The disposable pants comprise an upper section 12 configured to fasten around the waist 70 of the child through one or more fasteners 18. The disposable pants further comprise two leg portions 17, each with a terminal section 19 configured to enclose around the ankles of the child. In one embodiment, the terminal sections 19 include fasteners 20. A diaper is disposed within the pants, such that when the child urinates, the liquid contacts and is absorbed by a plurality of channels embedded within the interior of the crotch region of the diaper. Similarly, when the child defecates, a pocket disposed at the rear interior of the pants, proximal to the buttocks of the child, absorbs the solid waste and retains it in position until the diaper or pants are disposed of. Should the pocket and plurality of channels fail to absorb the solid and liquid waste, respectively, the inner lining of the pants is configured to additionally act as an absorbent receptacle for the liquid and solid waste.

It is therefore submitted that the instant invention has been shown and described in various embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. Disposable pants, consisting of:
    an upper section configured to encircle a wearer's waist;
    a front panel, an opposing back panel, two side edges disposed between the front panel and the opposing back panel, a crotch area, and a pair of leg receiving portions, each leg receiving portion defined on a side of the crotch area;

a pair of waist fasteners disposed on each side edge of the upper section so as to allow the upper section of the front panel to removably secure to the upper section of the back panel;

a front fastener centrally disposed on the upper section of the front panel;

a terminal section of each of the pair of leg portions ending in an elastic band configured to secure each leg receiving portion to a leg of the wearer;

a diaper disposed within an interior of the disposable pants;

the front fastener configured to receive a front end of the diaper;

a plurality of channels disposed within the diaper of the disposable pants configured to receive and absorb liquid therein;

one or more pockets disposed within the diaper of the disposable pants configured to receive and absorb human waste therein;

an inner lining composed of an absorbent material disposed on an inner surface of the disposable pants;

wherein the disposable pants are composed of a biodegradable material.

* * * * *